US009383314B2

(12) United States Patent
Malcolm et al.

(10) Patent No.: US 9,383,314 B2
(45) Date of Patent: Jul. 5, 2016

(54) MATURATION APPARATUS AND METHODS

(75) Inventors: Graeme P. Malcolm, Glasgow (GB);
Gareth T. Maker, Glasgow (GB);
Gordon Robertson, Glasgow (GB)

(73) Assignee: M SQUARED LASERS LIMITED,
Glasgow (GB)

( * ) Notice: Subject to any disclaimer, the term of this patent is extended or adjusted under 35 U.S.C. 154(b) by 0 days.

(21) Appl. No.: 14/232,030

(22) PCT Filed: Jul. 10, 2012

(86) PCT No.: PCT/GB2012/051621
§ 371 (c)(1),
(2), (4) Date: Jan. 10, 2014

(87) PCT Pub. No.: WO2013/008003
PCT Pub. Date: Jan. 17, 2013

(65) Prior Publication Data
US 2014/0160465 A1    Jun. 12, 2014

(30) Foreign Application Priority Data

Jul. 11, 2011    (GB) .................................... 1111837.9

(51) Int. Cl.
*G01J 5/00*        (2006.01)
*G01N 21/59*       (2006.01)
*C12H 1/22*        (2006.01)
*G01N 21/3504*     (2014.01)

(52) U.S. Cl.
CPC ................. *G01N 21/59* (2013.01); *C12H 1/22* (2013.01); *G01N 21/3504* (2013.01); *G01N 2021/3513* (2013.01); *G01N 2201/0227* (2013.01)

(58) Field of Classification Search
USPC .................................. 250/338.1; 356/51, 436
See application file for complete search history.

(56) References Cited

U.S. PATENT DOCUMENTS

| | | | |
|---|---|---|---|
| 98,784 A | 1/1870 | Marland et al. | |
| 2,865,770 A | 12/1958 | Nickol | |
| 2,943,940 A | 7/1960 | Wiedemann | |
| 3,001,877 A * | 9/1961 | Shapiro | 426/422 |
| 3,869,613 A * | 3/1975 | Link et al. | 250/343 |
| 5,473,161 A * | 12/1995 | Nix et al. | 250/343 |
| 6,603,555 B1 * | 8/2003 | Nanami et al. | 356/437 |
| 6,639,678 B1 * | 10/2003 | Veale | 356/437 |
| 7,212,955 B2 * | 5/2007 | Kirshenbau | 702/187 |
| 7,504,631 B2 * | 3/2009 | May | 250/339.1 |
| 7,528,372 B2 * | 5/2009 | Garvey et al. | 250/330 |

(Continued)

FOREIGN PATENT DOCUMENTS

| | | |
|---|---|---|
| EP | 0305973 | 3/1989 |
| EP | 0884584 | 12/1998 |

(Continued)

*Primary Examiner* — David J Makiya
*Assistant Examiner* — Taeho Jo
(74) *Attorney, Agent, or Firm* — Nixon & Vanderhye P.C.

(57) ABSTRACT

The invention provides an apparatus and a method that reduces fluid loss from a cask during a maturation process by sealably enclosing the cask in a vessel that provides an expansion volume to receive fluid vapor from the cask, a monitoring system and a method that monitors fluid loss from a cask during a maturation process using a light source and a detector to determine the presence of fluid vapor in the vicinity of the cask, a corresponding system for controlling a maturation process in which environmental conditions are controlled, and a cask leak testing system and method making use of the above.

44 Claims, 1 Drawing Sheet

(56) References Cited

U.S. PATENT DOCUMENTS

2003/0192368 A1* 10/2003 Kempe .................. 73/61.41
2007/0077176 A1* 4/2007 Lambert et al. ............ 422/82.05
2010/0067012 A1* 3/2010 Tondello et al. .............. 356/437
2010/0275784 A1 11/2010 Matesanz

FOREIGN PATENT DOCUMENTS

| EP | 1355147 | 10/2003 |
| FR | 2571382 | 4/1986 |
| GB | 191323548 | 12/2013 |
| WO | WO 2010136154 A1 * | 12/2010 |

* cited by examiner

MATURATION APPARATUS AND METHODS

This application is the U.S. national phase of International Application No. PCT/GB2012/051621 filed 10 Jul. 2012 which designated the U.S. and claims priority to GB Patent Application No. 1111837.9 filed 11 Jul. 2011, the entire contents of each of which are hereby incorporated by reference.

The present invention relates to apparatus and methods for use in maturation processes, and in particular apparatus and methods for reducing fluid loss from a cask during a maturation process, and apparatus and methods for controlling and for monitoring a maturation process. A particular embodiment provides a vessel to sealably enclose the cask and provide an expansion volume to receive fluid vapour from the cask.

BACKGROUND TO THE INVENTION

Scotch malt whisky production involves several stages, the most important of which is arguably the maturation process by which new-make whisky is matured for several years in wooden casks.

Whisky is typically ~60% water, ~40% ethanol (and ~0.1% other constituents), when it is casked, but during the maturation process (which typically takes ten to twenty years) a proportion of the fluid volume in the cask is lost to the atmosphere. This is affectionately referred to in the trade as the "angels' share".

The angels' share is, in Scotland, typically around 2% volume per annum. Elsewhere in the world the loss can be as high as 5% per annum. Some whisky producers may have tens of millions of whisky casks undergoing maturation at any one time so these losses are clearly significant.

In fact, the angels' share is reported to cost on the order of 10-15% of the production cost. It is therefore desirable to reduce or prevent this lost volume of product. Experiments have been conducted in which casks have been shrink-wrapped; however while fluid loss is eliminated (or significantly reduced) there is a corresponding elimination (or significant reduction) in air ingress which is believed to negatively affect the maturation process and hence the taste of the final product.

Wines, cognacs, armagnacs, sherries, ports, whiskeys (e.g. Bourbon) and beers may also be matured in barrels (as may balsamic vinegar), and the angels' share loss problem is also known to affect these maturation processes (to lesser or greater extents). This is therefore a wide reaching problem, and a solution that at least partially solves the problem will provide major economic benefits.

In view of the foregoing, it is an object of at least one embodiment of an aspect of the present invention to provide an apparatus that can reduce or prevent fluid loss during a maturation process, and a corresponding method.

It is also an object of at least one embodiment of an aspect of the present invention to provide a system for monitoring and/or controlling a maturation process, and a corresponding method.

SUMMARY OF THE INVENTION

According to a first aspect of the invention, there is provided an apparatus to reduce fluid loss from a cask during a maturation process, the apparatus comprising a vessel to sealably enclose the cask and provide an expansion volume to receive fluid vapour from the cask.

In conventional maturation processes, whisky casks (for example) leak ethanol vapour to the surrounding environment. By sealably enclosing the whisky cask and providing an expansion volume, ethanol vapour is initially able to leave the cask until the partial pressure of ethanol vapour (or other fluid lost from the cask) within the vessel reaches an equilibrium value at which there will be no further leakage.

Preferably, the apparatus further comprises a monitoring system arranged to monitor the presence of fluid vapour within the vessel.

The monitoring system permits monitoring of the leak rate as a function of time.

Preferably, the monitoring system comprises a light source and a detector, the detector arranged to receive light from the light source and the monitoring system configured to determine a relative transmission of the light through the vessel.

Preferably, the apparatus comprises at least one aperture in a wall of the vessel, the light source and detector arranged on opposite sides of the aperture. Preferably, the apparatus comprises two apertures located in walls of the vessel and defining an optical path through the vessel intersecting the light source and the detector. Alternatively, the apparatus further comprises a mirror arranged to receive and reflect light from the light source to the detector via a same aperture. Preferably, the at least one aperture comprises a window. For example, the window may comprise calcium fluoride ($CaF_2$).

Preferably, the light source comprises a laser source. Most preferably, the light source comprises an infrared laser source. Optionally, the light source comprises an optical parametric oscillator mid-infrared source. Alternatively, the light source comprises a quantum cascade laser source. The light source may be tuned to an absorption line or absorption band of ethanol. Alternatively, or additionally, the monitoring system comprises an active infrared hyperspectral imaging system.

Advantageously, the vessel comprises a lid. The lid and/or main body of the vessel may be provided with a rubber gasket or O-ring to provide a seal there between. Preferably, the vessel is rectangular. Alternatively, the vessel is cylindrical or cask-shaped.

Optionally, the vessel is sized to receive a plurality of casks. Alternatively, or additionally, the vessel is in fluid communication with one or more like vessels with or without respective monitoring systems.

According to a second aspect of the invention, there is provided a method of reducing fluid loss from a cask during a maturation process, the method comprising sealing the cask within a vessel having an expansion volume, and receiving fluid vapour from the cask in the expansion volume of the vessel.

Preferably, the method further comprises monitoring the presence of ethanol within the sealed vessel. Most preferably, the method further comprises monitoring the presence of water vapour within the sealed vessel.

Preferably, the method comprises obtaining a background measurement of the presence of ethanol within the sealed vessel. Preferably, the method comprises recording the presence of ethanol within the sealed vessel as a function of time.

Embodiments of the second aspect of the invention may include one or more features corresponding to features of the first aspect of the invention or its embodiments, or vice versa.

According to a third aspect of the invention there is provided a monitoring system to monitor fluid loss from a cask during a maturation process, the monitoring system comprising a light source and a detector, the detector arranged to receive light from the light source and the monitoring system arranged to determine the presence of fluid vapour in the vicinity of the cask.

Preferably, the light source comprises a laser source. Preferably, the light source comprises an optical parametric oscillator mid-infrared source. Alternatively, the light source comprises a quantum cascade laser source. The light source may be tuned to an absorption line or absorption band of ethanol.

Embodiments of the third aspect of the invention may include one or more features corresponding to features of the first or second aspects of the invention or its embodiments, or vice versa.

According to a fourth aspect there is provided a method of monitoring fluid loss from a cask during a maturation process, the method comprising emitting light from a light source, receiving light from the light source at a detector, and determining a relative transmission of the light in the vicinity of the cask.

Preferably, the method comprises locating one or both of the light source and detector proximal to the cask.

Embodiments of the fourth aspect of the invention may include one or more features corresponding to features of the first, second or third aspects of the invention or its embodiments, or vice versa.

According to a fifth aspect of the invention, there is provided a system for controlling a maturation process, the system comprising the apparatus of the first aspect and a control system configured to control environmental conditions within the sealed vessel.

Preferably, the vessel is sized to provide sufficient atmospheric oxygen for at least a portion of the maturation process. Alternatively, or additionally, the vessel is sized to provide sufficient water vapour for at least a portion of the maturation process.

Preferably, the system comprises at least one pump operable to control an ambient pressure within the vessel. Optionally, the pump is operable to maintain a target ambient pressure within the vessel.

Optionally, the system comprises one or more gas sources in fluid communication with the vessel, operable to control the presence of one or more gases within the vessel.

Preferably, the system further comprises one or more heating and/or cooling devices configured to control a temperature of the vessel.

Embodiments of the fifth aspect of the invention may include one or more features corresponding to features of the first to fourth aspects of the invention or its embodiments, or vice versa.

According to a sixth aspect of the invention, there is provided a method of controlling a cask maturation process, comprising sealing the cask within a vessel, and controlling environmental conditions within the sealed vessel.

Preferably, the method comprises controlling the temperature within the vessel.

Preferably, the method comprises controlling the atmospheric pressure within the vessel.

Optionally, the method comprises adding one or more gases to the vessel.

Advantageously, the method comprises adding one or more substances selected to simulate a geographic location during maturation.

Advantageously, the method comprises maintaining a positive atmospheric pressure within the vessel. Additionally, or alternatively, the method comprises controlling a partial pressure of water vapour within the vessel to control the relative loss of water versus ethanol from the cask.

Optionally, the method comprises periodically purging the vessel. This permits further gas exchange between the cask and the expansion volume in the vessel, most preferably after the equilibrium condition is reached.

Embodiments of the sixth aspect of the invention may include one or more features corresponding to features of any of the first to fifth aspects of the invention or its embodiments, or vice versa.

According to a seventh aspect of the invention, there is provided a cask leak testing system, comprising the apparatus of the first aspect, the system of the third aspect, or the system of the fifth aspect.

Optionally, the system comprises imaging means configured to obtain one or more images of the cask to identify the location and size of one or more leaks in the cask. Optionally, the imaging means comprises an active infrared hyperspectral imaging system.

Embodiments of the seventh aspect of the invention may include one or more features corresponding to features of any of the first to sixth aspects of the invention or its embodiments, or vice versa.

According to an eighth aspect of the invention, there is provided a method of testing a cask for leaks, comprising sealing the cask within a vessel of the first aspect and employing a monitoring system of the third aspect.

Preferably, the method comprises filling the cask with a test gas, and detecting the presence of the test gas within the expansion volume of the vessel using the monitoring system.

Embodiments of the eighth aspect of the invention may include one or more features corresponding to features of any of the first to seventh aspects of the invention or its embodiments, or vice versa.

BRIEF DESCRIPTION OF THE DRAWINGS

There will now be described, by way of example only, various embodiments of the invention with reference to the drawings, of which.

DETAILED DESCRIPTION OF PREFERRED EMBODIMENTS

The following example is described in the context of the maturation of whisky within a whisky cask, however it will be understood that the invention finds utility in other maturation processes; for example of wine, cognac, armagnac, sherry, port, whiskey (e.g. Bourbon), beer and balsamic vinegar. Furthermore, while wooden casks are typically employed it is understood that casks made from other materials (such as plastics or metals as increasingly used in wine maturation) shall not fall outside the scope of protection set out herein.

Figure 1:
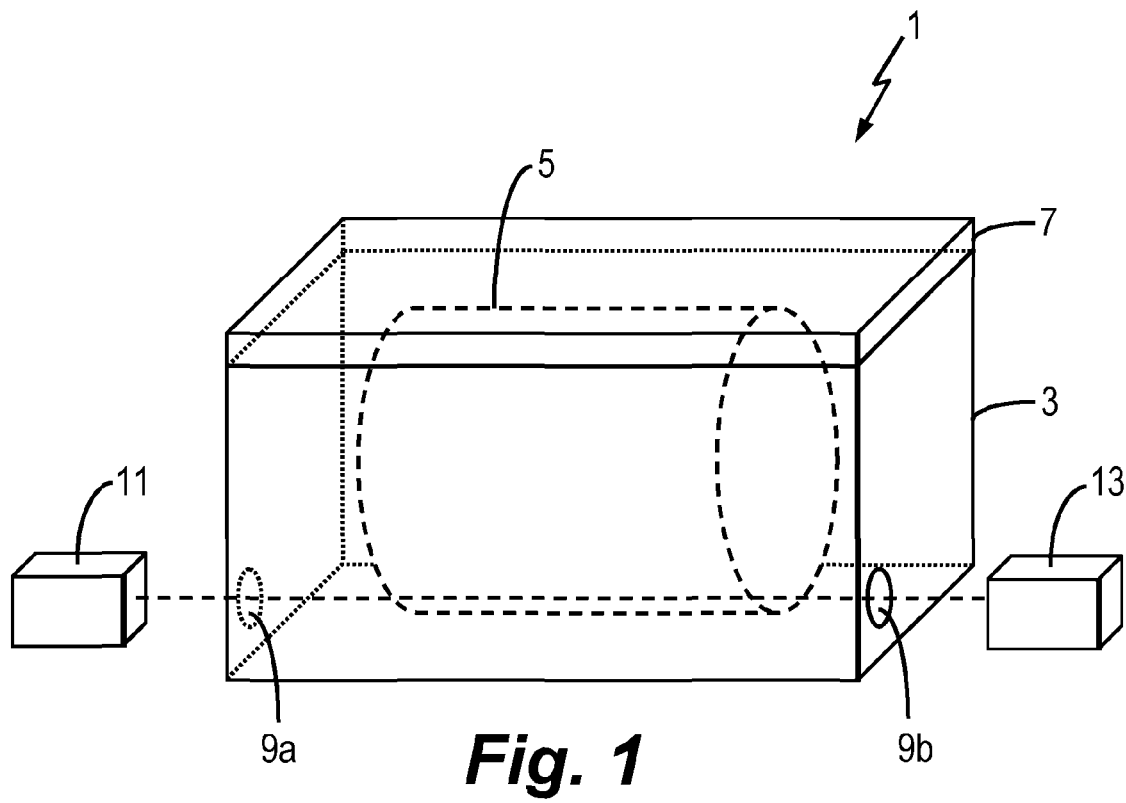
FIG. 1 illustrates in schematic form an apparatus to monitor and control whisky maturation process in accordance with an aspect of the present invention.

FIG. 1 illustrates an apparatus 1 for monitoring and controlling the whisky maturation process, comprising a vessel 3 to house a whisky cask 5. The vessel 3 is rectangular box, in this embodiment made of aluminium, and comprises a lid 7 to provide access to the vessel. The lid 7 is held in place using screws and has a rubber gasket (not shown) such that when the lid 7 is screwed down the vessel 3 is sealed. The vessel provides an expansion volume (i.e. the internal volume not occupied by the cask 5) into which vapour (e.g. ethanol vapour) from the cask may expand. As will be demonstrated below, experimental results show that this prevents further fluid loss from the cask once an equilibrium condition is reached.

Two apertures 9a, 9b are provided at opposing ends of the vessel, defining an optical path through the vessel. The apertures are sealed by way of calcium fluoride ($CaF_2$) windows affixed thereto, although any suitable material for the windows may be used.

Light from an infrared laser source 11, in this example a mid-infrared optical parametric oscillator source outputting 70 mW at approximately 3306 nm (although it will be readily apparent that any other suitable infrared light source may be employed), is directed through the apertures to a detector 13. This particular wavelength coincides with the O—H and C—H stretch absorption bands of ethanol, and accordingly transmission through the vessel gives an indication of the presence of ethanol within the vessel. The detector 13, in this case a laser power meter, is connected to a data logger (not shown), for example a PC with a suitable data acquisition card, to record transmitted power as a function of time.

In use, a background level for determining relative transmission or absorption is obtained without the cask 5 present in the vessel 3, although the background measurement could be taken immediately after the cask 5 is placed in the vessel 3 (before or after the lid 7 is in place) before any significant ethanol leakage occurs. Subsequently, the lid 7 is secured in place, creating a seal. As noted above, ethanol will leak out of the cask 5 in the form of ethanol vapour, which results in absorption of the laser light within the vessel 3. This absorption is detected by way of a reduction in optical power through the vessel 3, detected by the detector 13.

It is envisaged that an alternative embodiment of the invention comprises the laser source and power meter housed inside the vessel, in which case the apertures are not required. It is also envisaged that the monitoring system of the invention may be employed as a stand-alone monitoring system separate from a vessel, and employed to monitor fluid loss from a cask by detecting the presence of, say, ethanol vapour proximal to the cask.

Figure 2:
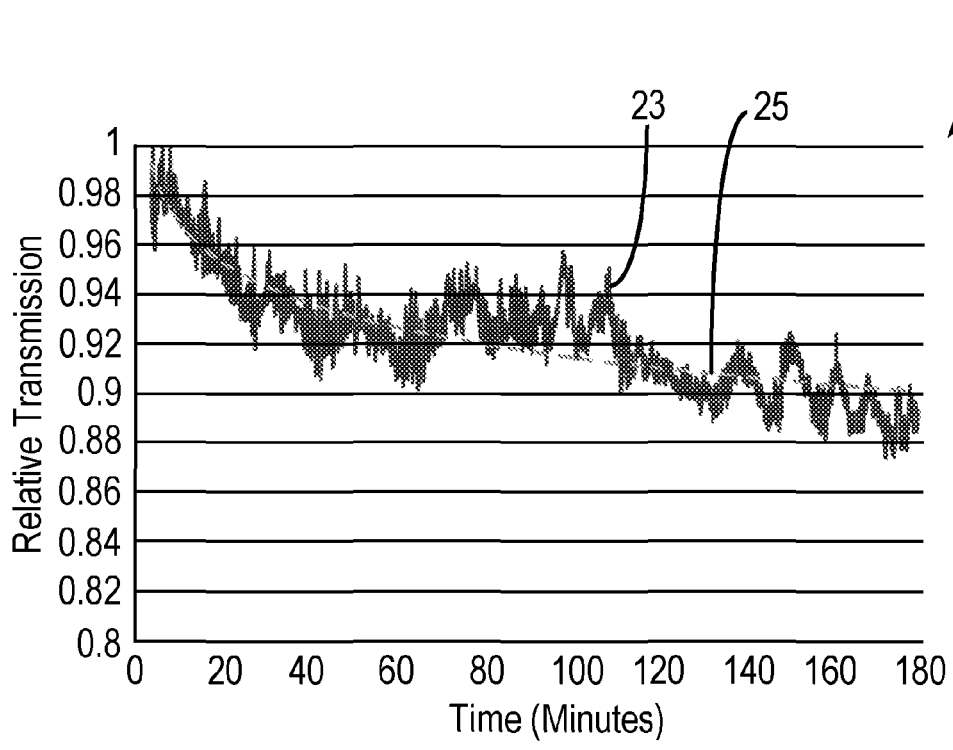
FIG. 2 is a graph of relative transmission of a light beam directed through the apparatus illustrated in FIG. 1 versus time, during the initial stages of a maturation process, in accordance with an aspect of the present invention.

FIG. 2 illustrates an exemplary graph 21 of relative transmission 23 as a function of time, illustrating the leak rate of ethanol vapour from a test cask (5) housed within a vessel. Relative transmission is determined by dividing the measured optical power at time t with the background measurement obtained at the start of the process.

The applicant has noted that the leak rate decays over time, tending towards a plateau or continuum value at which leakage from the cask will cease. Extrapolation of a fit to the experimental data, indicated by reference number 25, in this example indicates that equilibrium would be reached within two to three days. At this stage the leakage from the cask has stopped and the amount of ethanol vapour is fixed.

It is envisaged that instead of two apertures providing a pass-through, a single aperture may be provided with a retro-reflecting mirror inside the vessel—for example on the opposing side of the vessel from the single aperture. The advantage would be two-fold; the absorption pathlength (and hence, sensitivity) would be doubled and the vessel could be monitored from one side.

The whisky cask 5 is shown sitting horizontally within the vessel, however it will be understood that the cask 5 may sit vertically or at any other orientation. Furthermore, while the vessel 3 is illustrated as being a rectangular box, any other suitable shape of container may be employed. For example, it may be useful to be cylindrical or cask-shaped in order to conform to existing storage facilities. Furthermore, while the vessel of this exemplary embodiment has been described as comprising aluminium, any other suitable material may be employed.

Of course a vessel may be sized to accommodate multiple whisky casks; a particular advantage being that the maturation process can be monitored and controlled for all said whisky casks at once, thus improving consistency of product between casks. Alternatively, several vessels could be linked by conduits such that conditions are shared throughout, whereupon a single one of said vessels could be monitored as described herein in the knowledge that conditions within or changes made to that vessel will correspond with or result in corresponding changes in conditions in the linked vessels.

While the exemplary embodiment has been described as monitoring the presence of ethanol within the vessel volume using a laser and a power meter, other useful information may be gleaned by employing a spectrometer or spectrophotometer to analyse the atmospheric composition within the vessel. The spectrometer may be of any suitable kind, for example a tuneable diode laser absorption spectrometer or an active infrared hyperspectral imaging system such as the Applicant's intra-cavity optical parametric oscillator based system. Thus, a detailed analysis of the composition of the atmosphere within the vessel might be determined in real-time.

The foregoing description of the invention provides an apparatus and a method that first and foremost prevents fluid loss from the cask once an equilibrium position has been reached.

By addition of a monitoring means, such as a light source and corresponding detector, the apparatus and method also allows the level of ethanol vapour leaking from the cask to be monitored. Optionally, the atmospheric composition can also be determined. The cask is also protected from external influences such as airborne pollutants.

Furthermore, the invention provides for a system and a method for controlling the maturation process. It has been found that simply sealing casks, for example by shrink-wrapping, does eliminate fluid loss however it also affects the maturation process because ingress of air into the cask from the surroundings is also prevented. This is expected to be of significant detriment to the taste of the whisky—whisky should be allowed to "breathe" as it matures.

To remedy this issue, the vessel provides an expansion volume. Furthermore, environmental conditions within the vessel 3, and particularly the expansion volume, can be controlled throughout the maturation period. The system comprises a control system that allows the pressure within the vessel 3 to be controlled, as well as the relative humidity and atmospheric composition and of course temperature. This control may comprise maintaining the same environmental conditions throughout an entire maturation process or alternatively varying the environmental conditions as required. By controlling the environmental conditions the maturation process of the whisky can also be controlled.

It is envisaged that substances may be added to the vessel during the maturation process to simulate desirable atmospheric conditions. For example, salt water could be injected to simulate the sea air of a shore-side maturation location.

In a particular embodiment of the invention, the control system is used to maintain a small positive atmospheric pressure within the sealed vessel. Accordingly, the fluid loss from the cask resulting from the angels' share is minimised while still allowing for air (oxygen) ingress into the cask to allow the whisky to mature properly.

As an extension of this embodiment, the vessel may be sized to provide sufficient atmospheric oxygen for an entire maturation process or portion thereof. As described above, the partial pressure of ethanol within the vessel resulting from the angels' share will plateau over the course of, say, a few days yet proper oxygenation is provided for over the course of a number of years. If necessary, the vessel can be purged and refilled every few years. Even with regular purging, the anticipated loss to the angels' share will be significantly reduced over the entire maturation process.

By way of example, it is found that the ratio of water loss to ethanol loss from a cask is dependent on the prevailing atmospheric conditions; principally relative humidity and temperature, although other conditions may also have an effect. For example, higher temperatures are found to increase losses of both ethanol and water. Higher humidity results in increased ethanol loss (relative to water) and lower humidity results in increased water loss (relative to ethanol). The system described herein allows these conditions (temperature and relative humidity) to be controlled, thus controlling the maturation process.

One particular use for this system will be in the event that testing during the maturation process reveals some issue with the whisky that can be remedied by varying the atmospheric conditions. For example, if it was deemed that increased water loss was required, relative humidity could be reduced. In this way, a specific ethanol content can be targeted, particularly during the final stages of the maturation process. This may, for example, be used to increase alcohol content of whisky or to reduce the alcohol content of wine in the final product—as is often required in the industry.

A further application of the present invention is to detect leaks in a cask, whereby the cask is inserted into the vessel and leakage into the vessel monitored as a function of time to determine the presence of a leak and quantify the extent of the leak. This is preferably carried out before filling with whisky—for example by filling with a test gas. It is envisaged that imaging systems (such as the applicant's active infrared hyperspectral imaging system) may be employed to identify the location and/or the size of any leaks in the cask.

The invention provides an apparatus and a method that reduces fluid loss from a cask during a maturation process by sealably enclosing the cask in a vessel that provides an expansion volume to receive fluid vapour from the cask, a monitoring system and a method that monitors fluid loss from a cask during a maturation process using a light source and a detector to determine the presence of fluid vapour in the vicinity of the cask, a corresponding system for controlling a maturation process in which environmental conditions are controlled, and a cask leak testing system and method making use of the above.

Various modifications may be made within the scope of the invention as herein intended, and embodiments of the invention may include combinations of features other than those expressly claimed. For example, and as stated above, while specific examples are described in relation to the maturation of whisky in casks, similar apparatus, methods and systems may be employed in the maturation of bourbon and other spirits, wines, other alcoholic beverages, and other fluids (e.g. balsamic vinegar) that are matured in casks.

The invention claimed is:

1. An apparatus to reduce fluid loss from a cask during a maturation process, the apparatus comprising:
a vessel to sealably enclose the cask and provide an expansion volume to receive fluid vapour that has escaped from the cask; and
a monitoring system arranged to monitor the presence of the fluid vapour in the expansion volume within the vessel that has escaped from the cask;
wherein the monitoring system comprises a light source and a detector, the detector arranged to receive light from the light source and the monitoring system configured to determine a relative transmission of the light through the vessel.

2. The apparatus according to claim 1, wherein the monitoring system is configured to monitor fluid vapour leak rate as a function of time.

3. The apparatus according to claim 1, wherein the apparatus comprises at least one aperture in a wall of the vessel, the light source and detector arranged on opposite sides of the aperture.

4. The apparatus according to claim 3, wherein the at least one aperture comprises a window.

5. The apparatus according claim 4, wherein the window comprises $CaF_2$.

6. The apparatus according to claim 1, wherein the apparatus comprises two apertures located in walls of the vessel and defining an optical path through the vessel intersecting the light source and the detector.

7. The apparatus according to claim 1, wherein the apparatus further comprises a mirror arranged to receive and reflect light from the light source to the detector via a same aperture.

8. The apparatus according to claim 1, wherein the light source comprises a laser source.

9. The apparatus according to claim 1, wherein the light source comprises an infrared laser source.

10. The apparatus according to claim 1, wherein the light source comprises an optical parametric oscillator mid-infrared source.

11. The apparatus according to claim 1, wherein the light source comprises a quantum cascade laser source.

12. The apparatus according to claim 1, wherein the light source is tuned to an absorption line or absorption band of ethanol.

13. The apparatus according to claim 1, wherein the monitoring system comprises an active infrared hyperspectral imaging system.

14. The apparatus according to claim 1, wherein the vessel comprises a lid.

15. The apparatus according to claim 14, wherein the lid and/or main body of the vessel is provided with a rubber gasket or O-ring to provide a seal there between.

16. The apparatus according to claim 1, wherein the vessel is rectangular.

17. The apparatus according to claim 1, wherein the vessel is cylindrical or cask-shaped.

18. The apparatus according to claim 1, wherein the vessel is sized to receive a plurality of casks.

19. The apparatus according to claim 1, wherein the vessel is in fluid communication with one or more like vessels with or without respective monitoring systems.

20. A system for controlling a maturation process, the system comprising the apparatus of claim 1 and a control system configured to control environmental conditions within the sealed vessel.

21. The system according to claim 20, wherein the vessel is sized to provide sufficient atmospheric oxygen for at least a portion of the maturation process.

22. The system according to claim 20, wherein the vessel is sized to provide sufficient water vapour for at least a portion of the maturation process.

23. The system according to claim 20, wherein the system comprises at least one pump operable to control an ambient pressure within the vessel.

24. The system according to claim 23, wherein the pump is operable to maintain a target ambient pressure within the vessel.

25. The system according to claim 20, wherein the system comprises one or more gas sources in fluid communication with the vessel, operable to control the presence of one or more gases within the vessel.

26. The system according to claim 20, wherein the system further comprises one or more heating and/or cooling devices configured to control a temperature of the vessel.

27. A cask leak testing system, comprising the apparatus of claim 1.

28. The cask leak testing system according to claim 27, further comprising imaging means configured to obtain one or more images of the cask to identify the location and size of one or more leaks in the cask.

29. The cask leak testing system according to claim 27, wherein the imaging means comprises an active infrared hyperspectral imaging system.

30. A method of testing a cask for leaks, comprising sealing the cask within a vessel of claim 1.

31. The method according to claim 30, further comprising filling the cask with a test gas, and detecting the presence of the test gas within the expansion volume of the vessel using the monitoring system.

32. A method of reducing fluid loss from a cask during a maturation process, the method comprising:
sealing the cask within a vessel having an expansion volume, and receiving fluid vapour from the cask in the expansion volume of the vessel;
monitoring the presence of the fluid vapour within the expansion volume of the vessel that has escaped from the cask using a light source and a detector, the detector arranged to receive light from the light source; and
determining a relative transmission of the light through the vessel.

33. The method according to claim 32, further comprising monitoring the presence of ethanol within the sealed vessel.

34. The method according to claim 32, further comprising monitoring the presence of water vapour within the sealed vessel.

35. The method according to claim 32, further comprising obtaining a background measurement of the presence of ethanol within the sealed vessel.

36. The method according to claim 32, further comprising recording the presence of ethanol within the sealed vessel as a function of time.

37. A method of controlling a cask maturation process, comprising sealing the cask within a vessel, controlling environmental conditions within the sealed vessel, and monitoring the presence of the fluid vapour within the vessel using a light source and a detector, the detector arranged to receive light from the light source; and determining a relative transmission of the light through the vessel.

38. The method according to claim 37, further comprising controlling the temperature within the vessel.

39. The method according to claim 37, further comprising controlling the atmospheric pressure within the vessel.

40. The method according to claim 37, further comprising adding one or more gases to the vessel.

41. The method according to claim 37, further comprising adding one or more substances selected to simulate a geographic location during maturation.

42. The method according to claim 37, further comprising maintaining a positive atmospheric pressure within the vessel.

43. The method according to claim 37, further comprising controlling a partial pressure of water vapour within the vessel to control the relative loss of water versus ethanol from the cask.

44. The method according to claim 37, further comprising periodically purging the vessel.

* * * * *